United States Patent
Butler et al.

[11] Patent Number: 5,358,698
[45] Date of Patent: Oct. 25, 1994

[54] APPARATUS FOR DEHYDROGENATION OF ETHYLBENZENE TO STYRENE

[75] Inventors: James R. Butler; Thomas W. Johnston, both of Houston, Tex.

[73] Assignee: Fina Technology, Inc., Dallas, Tex.

[21] Appl. No.: 661,359

[22] Filed: Feb. 26, 1991

[51] Int. Cl.$^5$ .............................. B01J 8/02
[52] U.S. Cl. ................. 422/218; 422/219; 422/220
[58] Field of Search ........... 422/218, 220, 211, 219, 422/222

[56] References Cited

U.S. PATENT DOCUMENTS 3,597,166  8/1971  Hochman .................... 422/220
4,318,894  3/1982  Hensel et al. ............... 422/220
4,471,821  9/1984  Coulon et al. ............... 422/220

Primary Examiner—Robert J. Warden
Assistant Examiner—Christopher Y. Kim
Attorney, Agent, or Firm—Michael J. Caddell; M. Norwood Cheairs

[57] ABSTRACT

A catalyst-bed radial gas-flow reactor system is disclosed utilizing a generally cylindrical catalyst bed located in an annualar area between an outer reactor shell and a generally coaxially located displacement member; wherein the gas flow through the reactor is optimized to extend catalyst life by including a non-cylindrical section in at least a portion of the displacement cylinder, and the gas-supply duct entering the reactor shell has baffling arranged to equalize flow velocities across the reactor diameter.

1 Claim, 18 Drawing Sheets

APPARATUS FOR DEHYDROGENATION OF ETHYLBENZENE TO STYRENE

BACKGROUND OF THE INVENTION

This invention relates to the field of styrene manufacture and more particularly discloses apparatus including reactor vessels for the dehydrogenation of ethylbenzene into styrene monomer.

It is well known in the art of styrene manufacture to react ethylbenzene over a dehydrogenation catalyst such as iron oxide under elevated temperatures in the range of around 1000° F. and at a pressure of about 10 to 20 PSIA in order to strip hydrogen from the ethyl-radical on the benzene ring to form the styrene molecule. This is normally done in a styrene radial reactor which also is commonly termed an EB dehydro reactor. The dehydro reactors generally are elongated cylindrical vertical structures of a very large size ranging in diameter from about five to thirty feet or more and in length from about ten to one hundred feet or more. The normal construction for such a reactor allows for input of the ethylbenzene gas at an inlet located in the bottom center of the vertical reactor, whereupon the gas is flowed up through an annular area, passing radially outward through a porous catalyst bed of iron oxide or other suitable dehydro catalyst, and then passing upward through an outer annular area to exit at the top of the reactor shell. Since the flow of ethylbenzene across the catalyst bed is in a radial direction, these reactors are sometimes identified as "radial" reactors.

Normally a radial reactor would be sized such that the annular flow area inside the catalyst bed would have some relative proportional value with respect to the cross-sectional flow area of the inlet pipe delivering ethylbenzene to the reactor. Preferably the annular flow area inside the catalyst bed would be larger than the cross-sectional flow area of the flow inlet pipe. Because of the extended vertical length of such reactors, normally the inlet pipe to the bottom of the reactor must come in at a relatively sharp ninety degree radius and the resulting effect is a side-to-side maldistribution of flow across the reactor vessel. Ideally, the inlet pipe to the reactor would be a straight vertical pipe for a considerable distance prior to entering the reactor, but due to physical configurations, this is not possible because of the extended vertical height of the reactor.

Also, due to the nature of flow across the extended vertical length of the reactors, switching from longitudinal or axial flow into radial or transverse flow and then back into longitudinal flow, flow velocities across the catalyst bed from top to bottom vary widely in conventional reactor vessels, thus resulting in degraded catalyst life in those areas of the reactor with the greatest flow velocities. It has been found by experimentation and flow velocity measurements that the highest feed velocity across the catalyst beds in a radial reactor generally occurs near the top of the reactor, and the lowest velocity across the catalyst bed occurs near the bottom of the reactor near the inlet pipe. This increased velocity at the top of the catalyst bed and reduced velocity at the bottom of the catalyst bed results in a greatly shortened life of the catalyst near the top of the reactor and forces a shutdown of the reactor for catalyst regeneration much sooner than normally desirable.

SUMMARY OF THE INVENTION

The present invention discloses dehydrogenation reactor vessel apparatus that utilizes specific baffling in the inlet pipe to reduce "east to west" flow differences across the reactor and further utilizes optimally configured concentric displacement cylinders inside the reactor to normalize "north to south" flow velocities within the reactor and across the catalyst bed.

DESCRIPTION OF THE PREFERRED EMBODIMENTS

Figure 1:
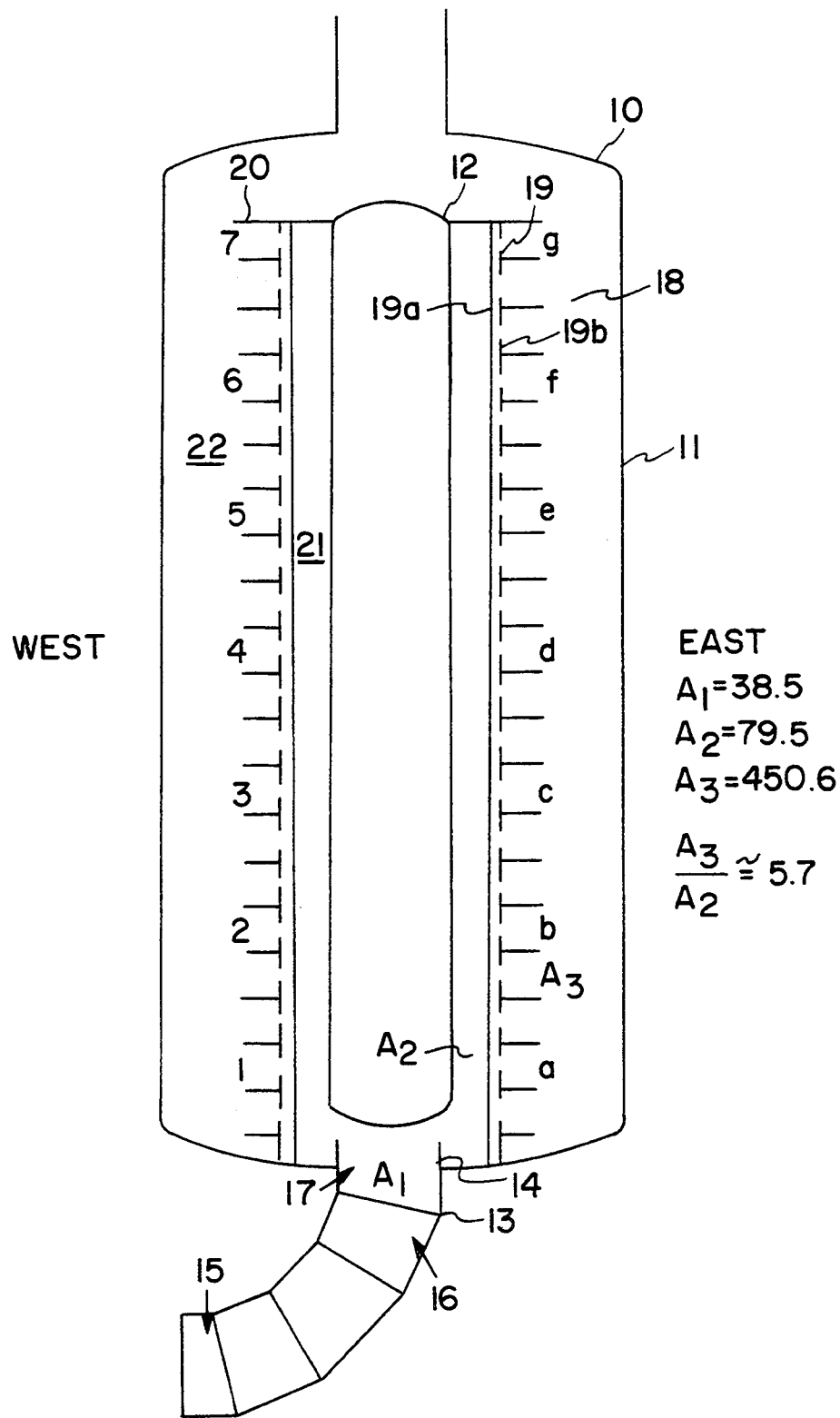
FIGS. 1 through 7 illustrate cross sectional schematic diagrams of the reactor vessel and inlet piping of the present invention.

FIG. 1 is a schematic cross sectional side view of an EB dehydro reactor vessel 10 having an elongated outer cylindrical shell 11 enclosing an inner cylindrical displacement member 12 located concentrically inside cylindrical vessel 11. Vessel 11 and displacement member 12 are generally right circular cylinders, meaning that a cross sectional view taken perpendicular to the longitudinal center lines of these two vessels would be circular in shape. Preferably, displacement cylinder 12 is located co-axially within vessel 11, meaning that the central longitudinal axis of the two cylindrical structures coincide. An inlet pipe 13 having a large cross sectional area is connected to a central inlet opening 14 formed in the bottom of shell 11. Preferably inlet pipe 13 is also cylindrical in cross sectional area and enters the vessel after making a ninety degree turn from horizontal. Inlet pipe 13 has a series of flow baffles 15, 16 and 17 attached internally to the walls thereof to control the flow of gas therethrough and offset the effect of the right angle turn in pipe 13.

The placement of cylinder 12 within vessel 10 in a coaxial alignment serves to form an annular catalyst area 18 therebetween. A cylindrical annular catalyst bed 19 is located between displacement cylinder 12 and wall 11 of cylinder 10. A series of optional radially outwardly extending flow baffles 20 may be formed on the outer wall of catalyst bed 19, extending radially outward therefrom to further direct flow of gases flowing through the catalyst bed and directing them into a radial flow direction, thereby preventing longitudinal flow and further smoothing out flow across the catalyst bed.

The catalyst bed 19 comprises a concentric cylindrical catalyst shell made of a perforated or porous inner wall 19a and a similar porous or perforated outer wall 19b. Preferably the catalyst shell is sufficient to maximize flow and still retain the dehydro catalyst between the inner and outer walls 19a and 19b. Some typical catalysts utilized in the dehydrogenation process are those sold by Shell Chemical Corporation and designated as Shell 105 and Shell 105E. These may be of the iron oxide type or other dehydrogenation types of catalysts.

The sizing of the flow areas of the inlet pipe 13 and the annular area 21 between the displacement cylinder 12 and the catalyst bed 19 is preferably in the range of about 2 to 1 with annular area 21 being approximately twice the value of the cross sectional area of pipe 13. Furthermore, the annular area 22 between catalyst bed 19 and vessel 11 is approximately five to six times the annular flow area 21.

Figure 2:
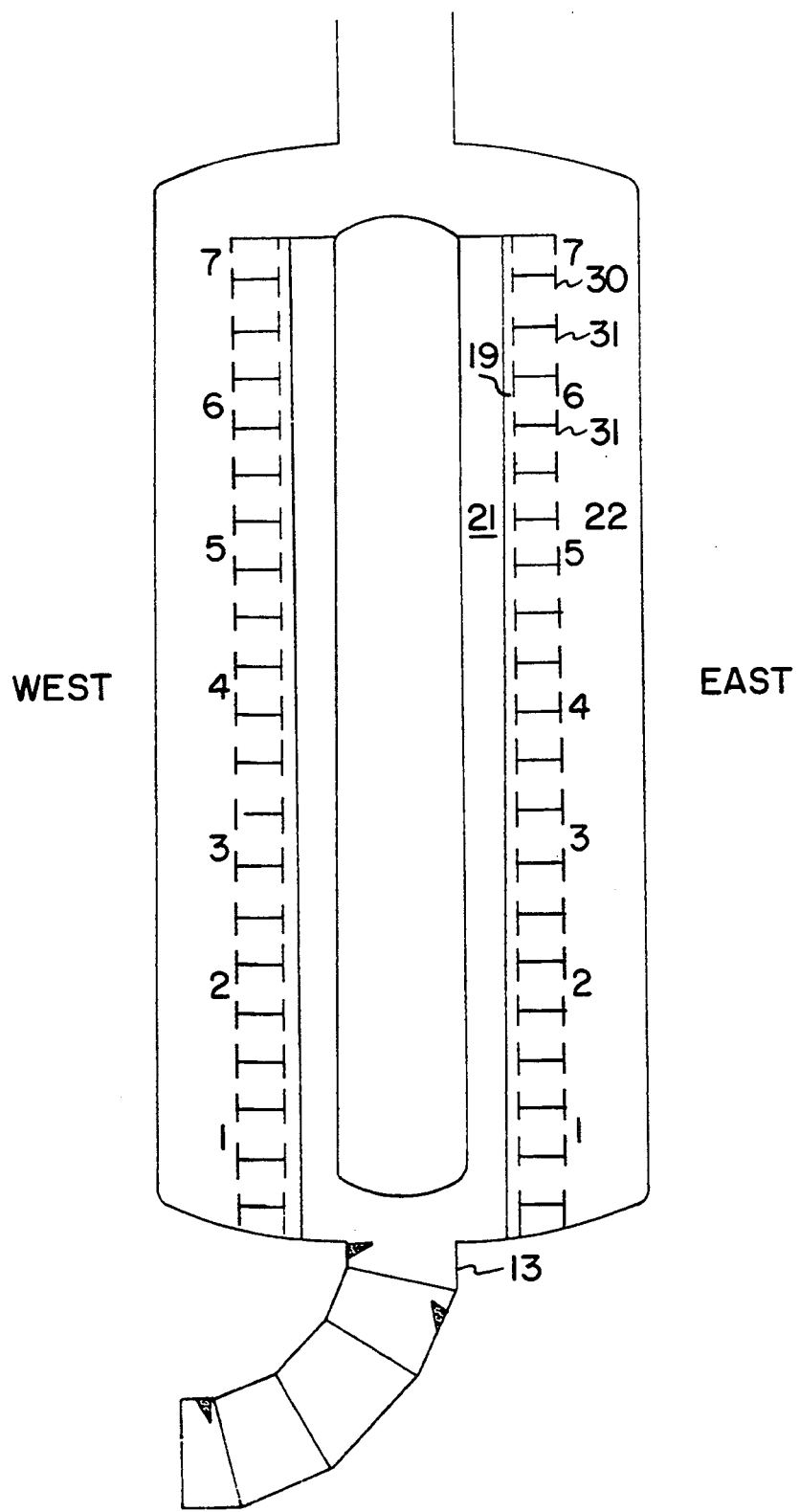

FIG. 2 is a side cross sectional schematic view of an alternate configuration of the reactor of FIG. 1. In FIG. 2, an optional outer baffle shell 30 has been added to the optional baffles 20 illustrated and described in FIG. 1. Baffle shell 30 comprises a series of radial orifices 31 passing through the wall thereof and communicating with outer annular flow area 22 from inner annular area 21 through catalyst bed 19.

The provision of outer baffle shell 30 with radial opening 31 provides a better source of flow control for the reactive gases passing through annulus 21 toward annulus 22. The conjunction of shell 30 and catalyst bed 19 directs the gases in a more radial flow direction and prevents the flow in the longitudinal axial direction.

Figure 3:
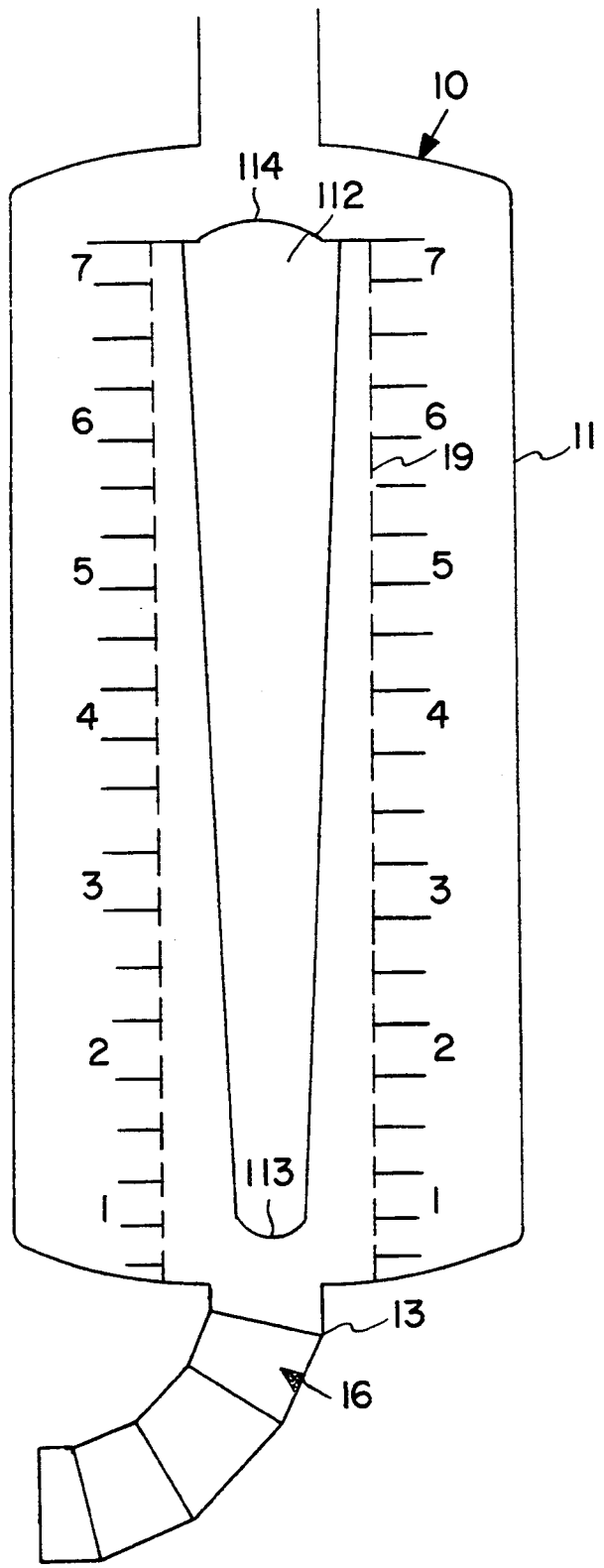

FIG. 3 is an alternate embodiment comprising a cross sectional side schematic view of an alternate displacement member construction. In FIG. 3 the displacement member 112, rather than being a cylindrical configuration, is a tapered frusto-conical configuration. The ratio of the upper diameter of displacement member 112 to the lower diameter is approximately 2:1. The remainder of the reactor system, with the exception of the inlet pipe, is the same. In this configuration the inlet pipe 13 has had flow baffles 15 and 17 removed and therefore retains only flow baffle 16. The reactor vessel outer shell 11 and the catalyst bed 19 remain relatively unchanged from FIG. 1.

The displacement member 112, as previously mentioned, comprises a frusto-conical section extending substantially from the bottom entirely the full length of the displacement member. Preferably the lower end 113 is a hemispherical configuration as is the upper end 114. The taper on the cylinder is substantially constant for the entire length and is an angle of taper of from about 1 degree up to about 15 degrees, with a preferable angle of approximately 2–4 degrees.

Figure 4:
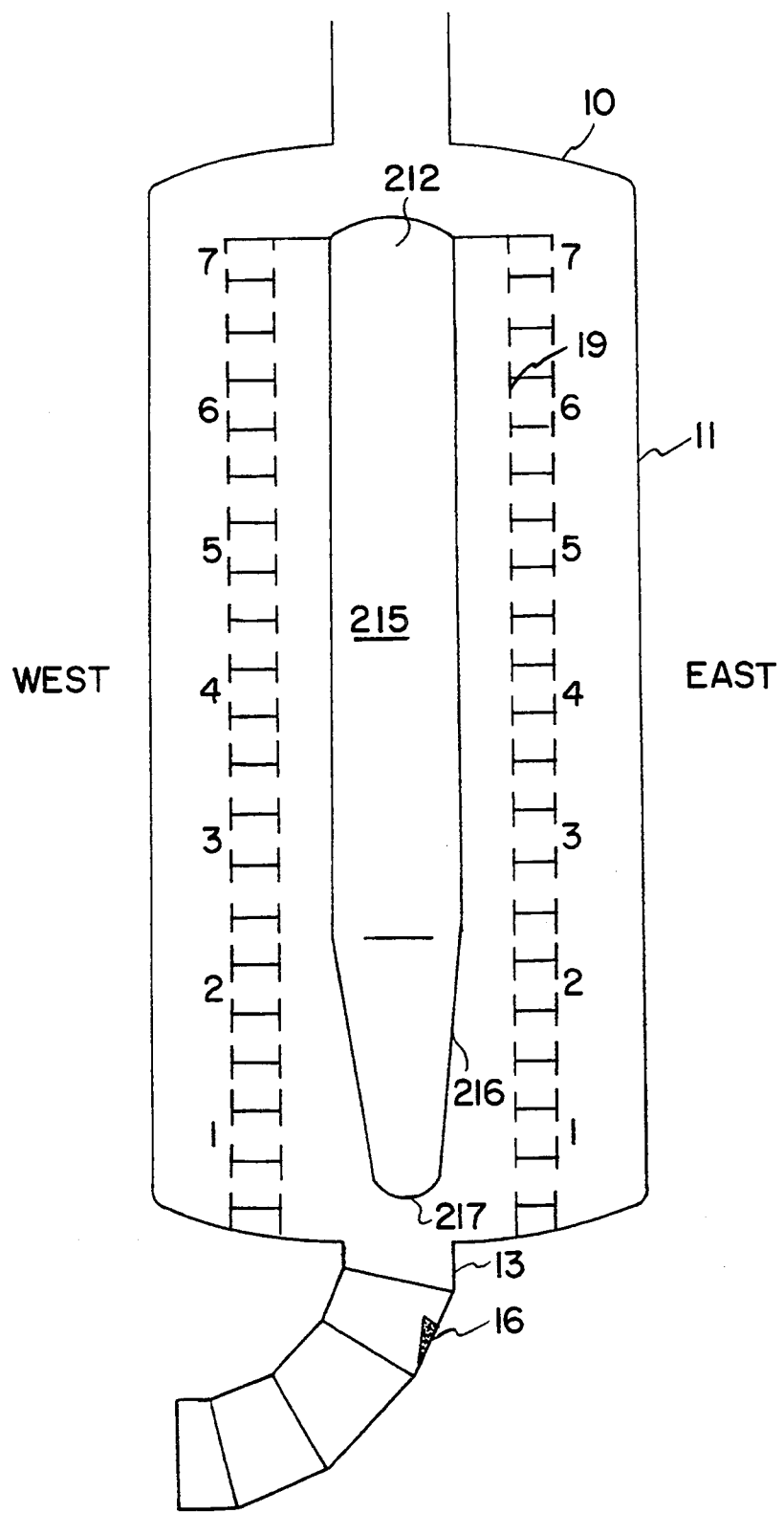

Yet another embodiment of the present invention is disclosed in FIG. 4 wherein the displacement member 212 comprises an upper portion 215 of a cylindrical nature and a lower portion 216 having a frusto-conical wall and a hemispherical bottom end to 217. The frusto-conical portion 216 of displacement member 212 comprises approximately one-fourth to one-third of the entire length of the displacement member. The angle of taper on the frusto-conical section 216 ranges from about 2 to about 30 degrees, and preferably about 4–10 degrees. The remainder of the reactor structure 10 is substantially identical to the previously described embodiment in FIG. 2.

Figure 5:
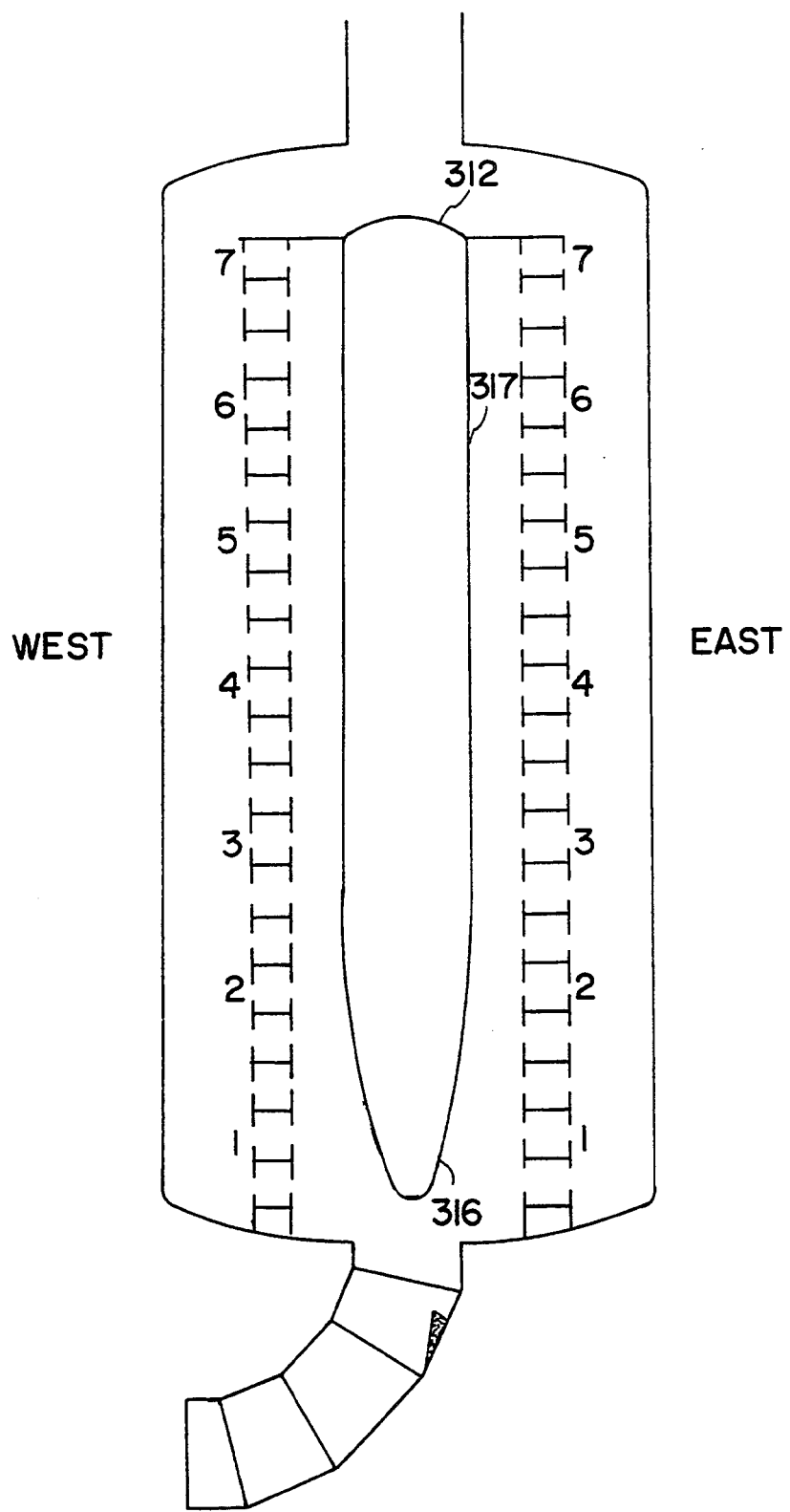

In another separate embodiment of the present invention, disclosed in cross sectional side view in FIG. 5, the displacement member designated 312 has the lower section formed in a parabolic configuration as indicated at 316. Section 316 a parabolic cross sectional configuration rotated about the central longitudinal axis to form a regular paraboloid end section 316 of consistent parabolic cross sectional configuration. The remainder of the displacement member 312 indicated at 317 comprises the same generally cylindrical portion as previously described in the other embodiments. Preferably the parabolic section 316 of member 312 comprises from one-fourth to one-third of the entire length of the member.

Figure 6:
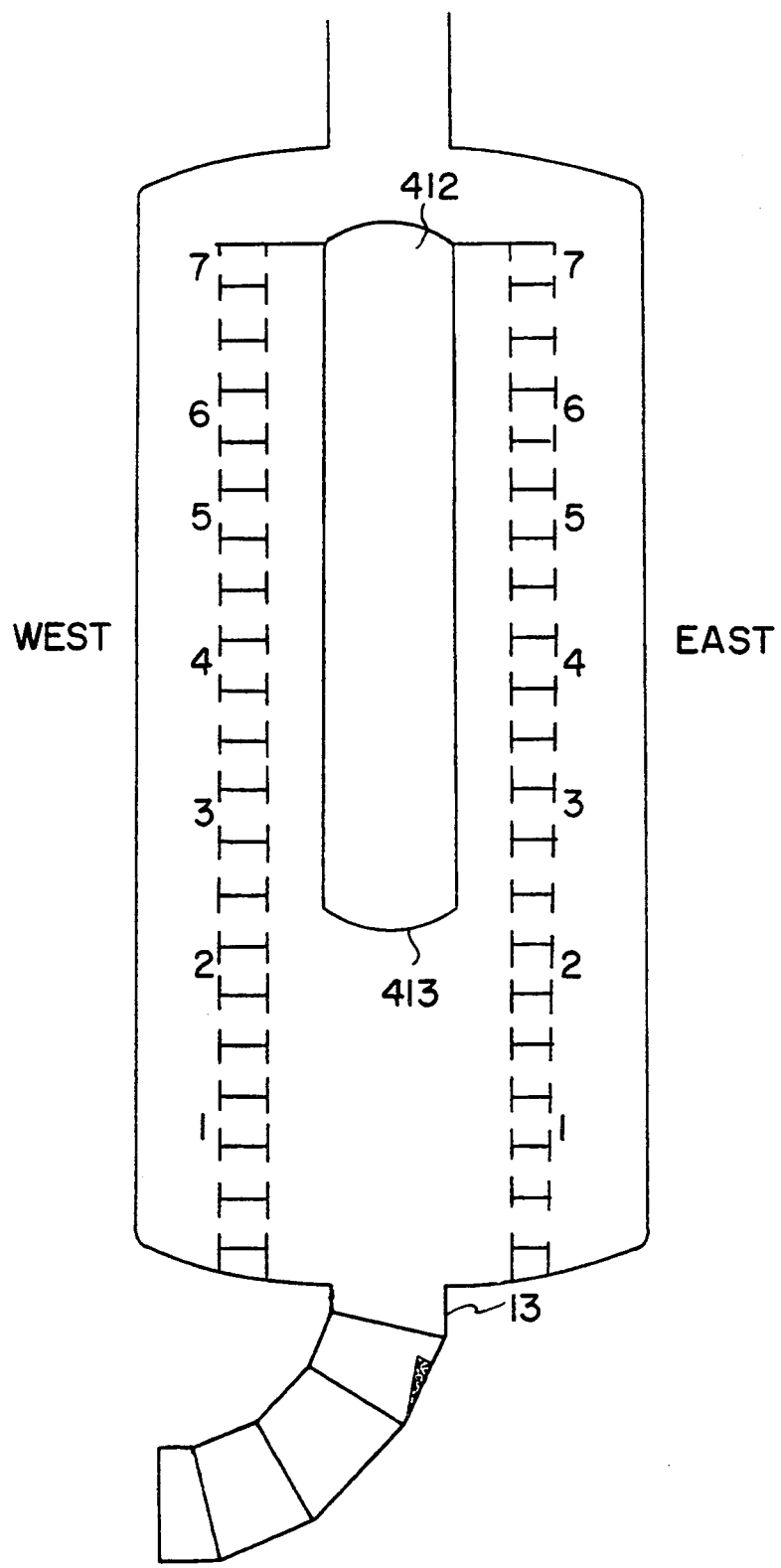

Yet another embodiment of the present invention is that disclosed in cross sectional side view illustrated in FIG. 6, in which the normally cylindrical displacement cylinder 412 has been shortened by approximately one-fourth to one-third of the length and results in a lower end 413 spaced a substantial distance above the inlet to the reactor.

Figure 7:
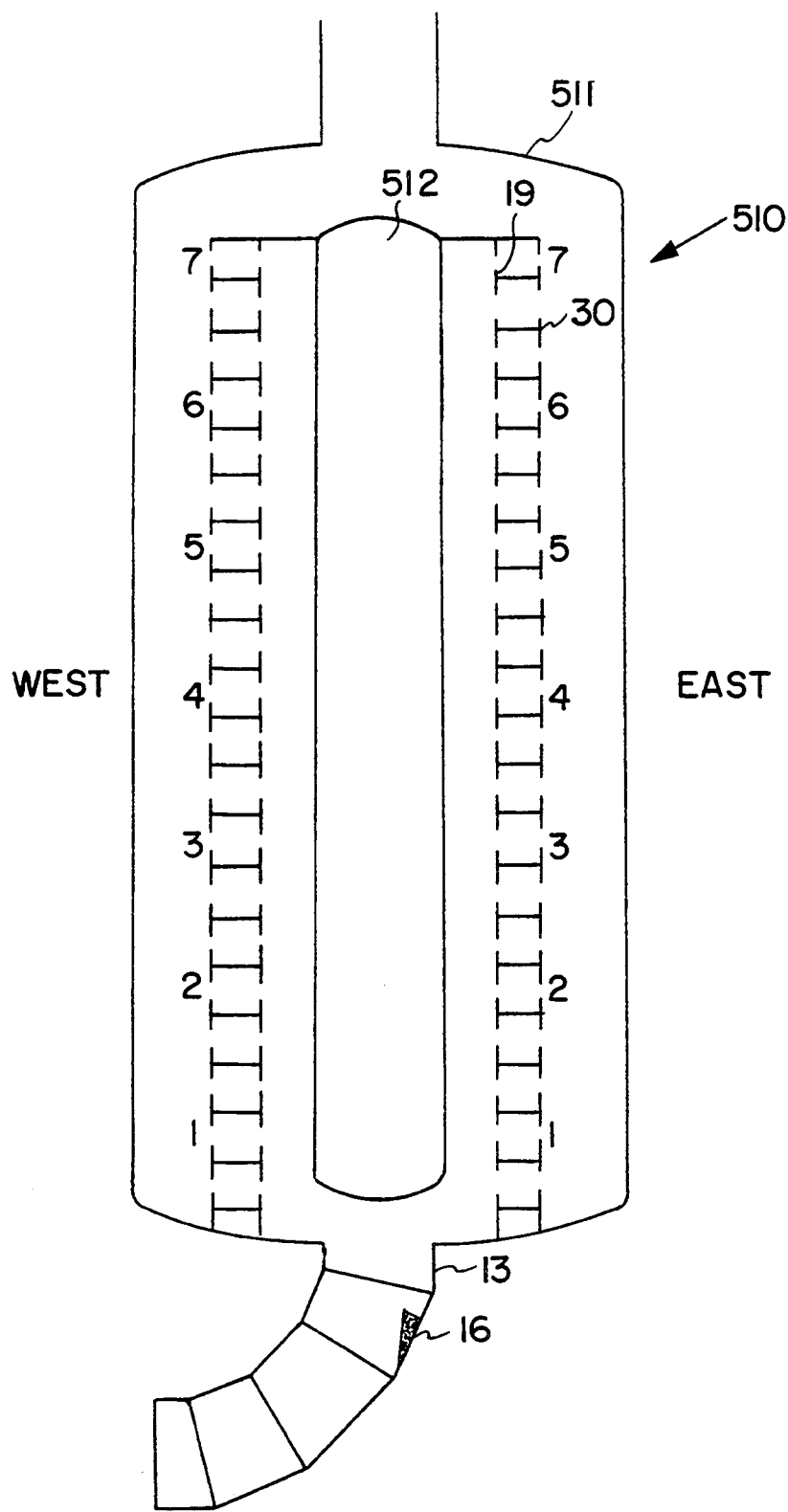

Referring now to FIG. 7, an even further embodiment of the reactor vessel is disclosed, wherein the normally flattened hemispherical top portion of the reactor 510 has been replaced by a frusto-conical top portion 511. The displacement member 512 is of the normal cylindrical configuration extending concentrically and coaxially down the center line of the reactor vessel 510. The remaining portions of the reactor assembly comprising the catalyst bed 19 and the baffle shell 30 are substantially identical to the previous embodiments of FIGS. 2. Likewise, the inlet pipe 13 containing the single flow baffle 16 is substantially identical to previously described embodiments of FIG. 3.

Figure 8:
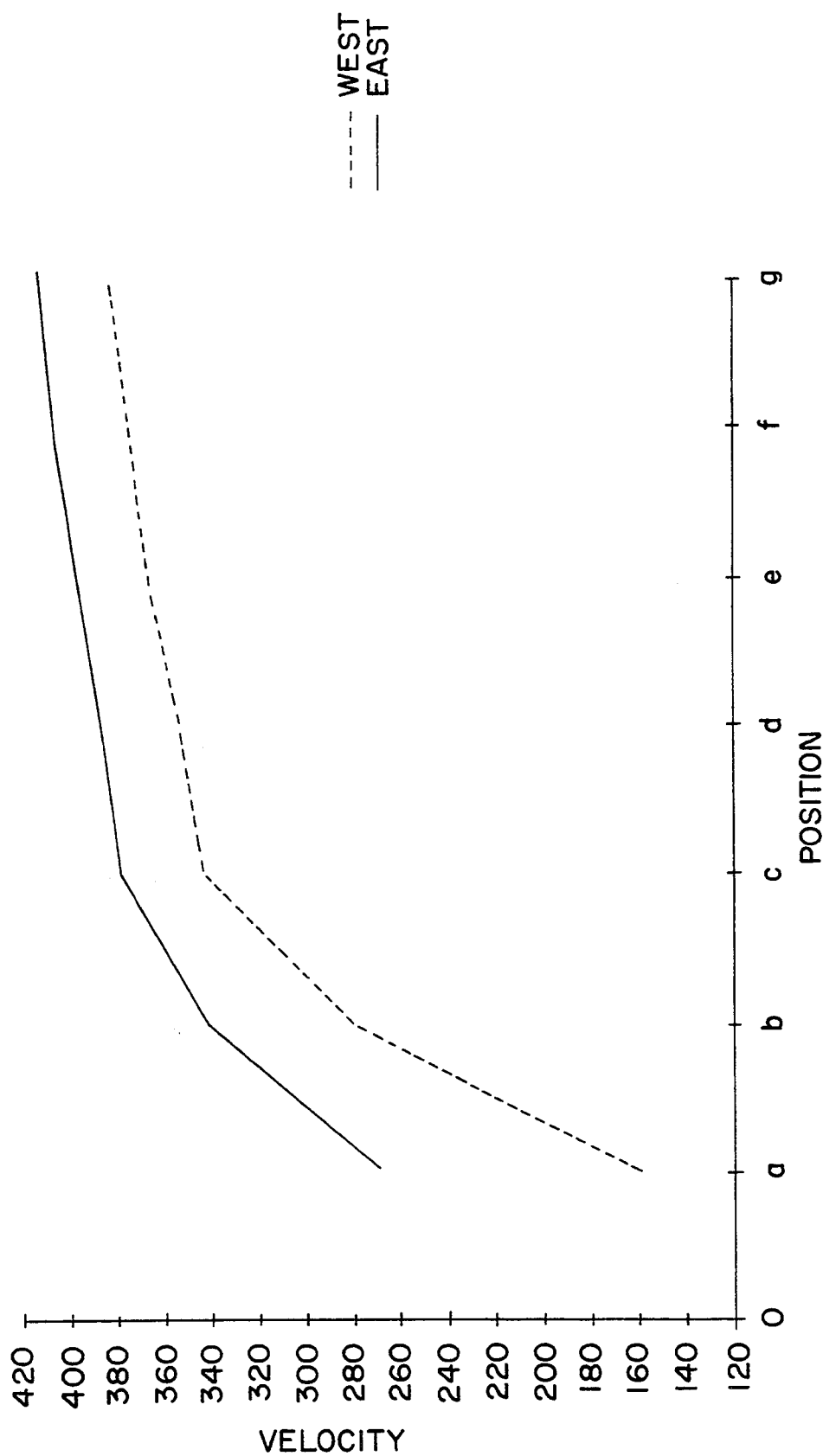
FIGS. 8 through 17 illustrate graphic comparisons of flow velocities at various positions in the various reactor designs of the present invention.

Referring now to the graph illustrated in FIG. 8, there is illustrated therein the relationship between flow velocity through the catalyst bed indicated on the left in feet per second, and the vertical position selected along the catalyst bed of FIG. 1. The vertical positions are indicated at equispaced intervals along the vertical configuration of the catalyst bed by the letters 1–7, beginning with 1 at the bottom of the catalyst bed and ending with 7 at the top of the catalyst bed. FIG. 8 represents the change in flow velocities moving from the bottom of the catalyst bed to the top of the catalyst bed. This indicates that a significant increase in flow occurs across the vertical gradient of the catalyst bed, going from approximately 160 to 420, a factor of over 2.5. FIG. 8 also discloses the difference in flow velocities between the east side and the west side of the reactor. It should be noted that in all figures the center line of the reactor vessel 10 is illustrated as lying in the plane of the figure. Likewise, the center line of supply pipe 13 lies in the plane of the figure and the ninety degree angle made by supply pipe 13 also lies in the plane of the figure.

For convention sake, the directional flow characteristics of the reactor caused by the vertical gradient of the catalyst bed and caused by the sharp turn in the supply pipe 13 can best be described by assigning directional connotations to the various asymmetrical portions of the reactor. Keeping in mind that the bend in the supply pipe 13 is a ninety degree bend lying in a single plane, that plane being the plane of the figure, the directional coordinates of the reactor are then assigned the same terminology as the points on a compass, with the top of the reactor being the north end, the bottom of the reactor being the south end and naturally the west side being the left side of the reactor and the right side being the east side of the reactor. This convention will be utilized in all descriptions of the present invention.

Referring back to FIG. 8, it can be seen that not only is there a substantial change in flow velocity from the bottom of the catalyst bed to the top of the catalyst bed, (keeping in mind that the flow being measured is the radial flow going from the inner annular area 21 to the outer annular area 22), but there is also a definite flow velocity change going from east to west, with the flow on the east side of the reactor being significantly higher than the flow at corresponding vertical points on the west side of the reactor.

In the diagram, the flow velocities on the east side of the reactor are represented by the solid line and the flow velocities at corresponding points on the west side of the reactor are designated with the dotted line. This convention also holds for all of the figures. Thus it can be seen from FIG. 8 that with the reactor configuration shown in FIG. 1 there is a very significant gradient of flow velocity across the vertical height of the catalyst bed as well as a difference in flow velocity from one side of the reactor to the other. It is believed that the flow velocity gradient from the top to the bottom of the reactor is the result of the relationship between the cross sectional annular areas and the displacement member 12. On the other hand, it is believed that the change in flow velocities from east to west is a result of the sharp angle in flow pipe 13, which result the inventors have attempted to modify by installation of flow baffles 15, 16, and 17.

Figure 9:
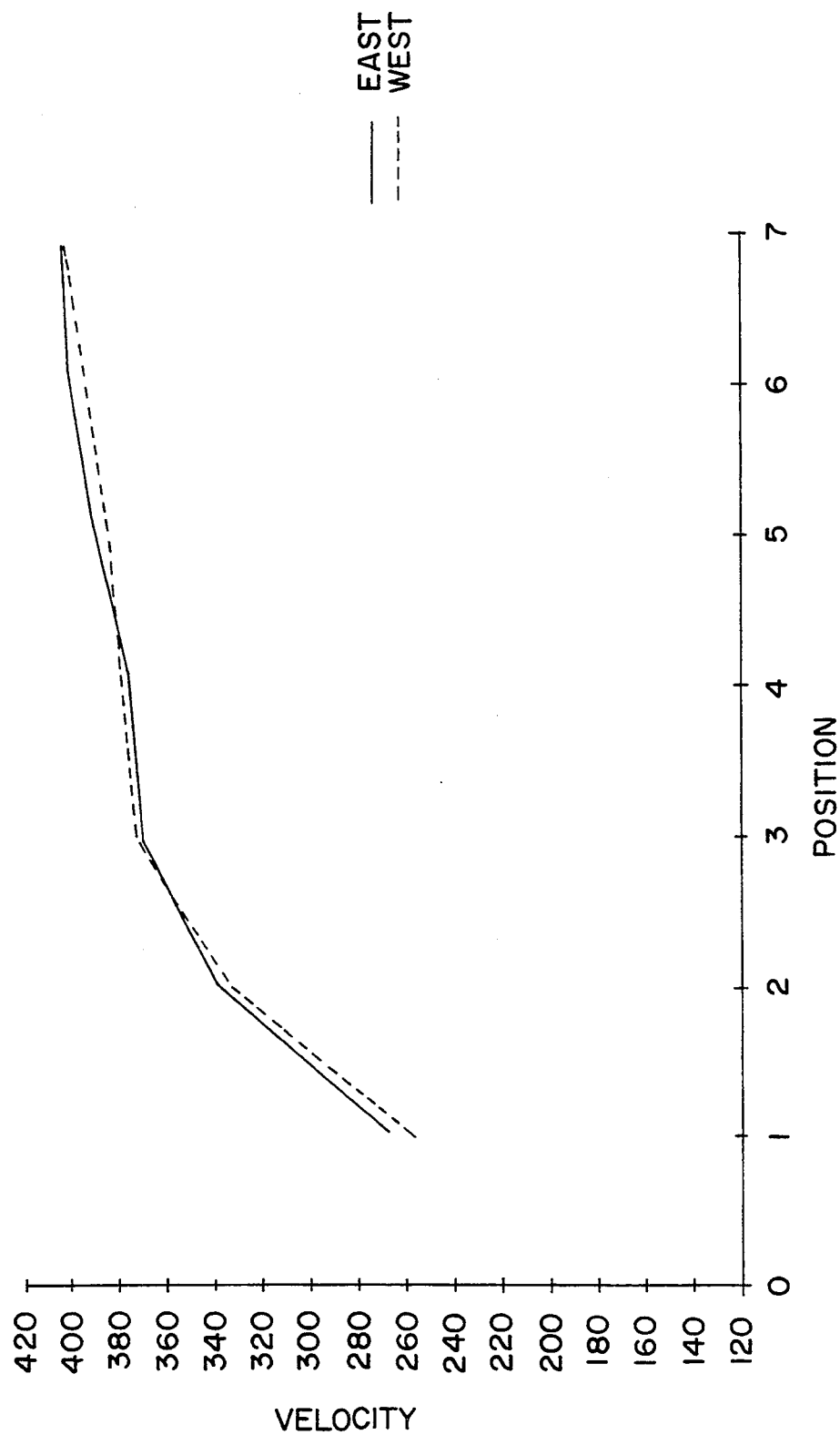

Referring now to FIG. 9 there is illustrated graphically the result of flow tests on the reactor configuration of FIG. 1 wherein the flow baffles 15 and 17 have been removed from flow pipe 13 leaving only flow baffle 16 in place. It is apparent from the substantially overlapping nature of the flow lines for the flow velocity graph lines for the east side of the reactor and the west side of the reactor that the placement of the single baffle 16 and removal of baffles 15 and 17 almost totally reduces any differential in flow velocities across the reactor from east to west. This is obviously a desirable result since it equalizes the flow velocities from east to west and thereby optimizes the catalyst life in a transverse direction across the catalyst bed.

Figure 10:
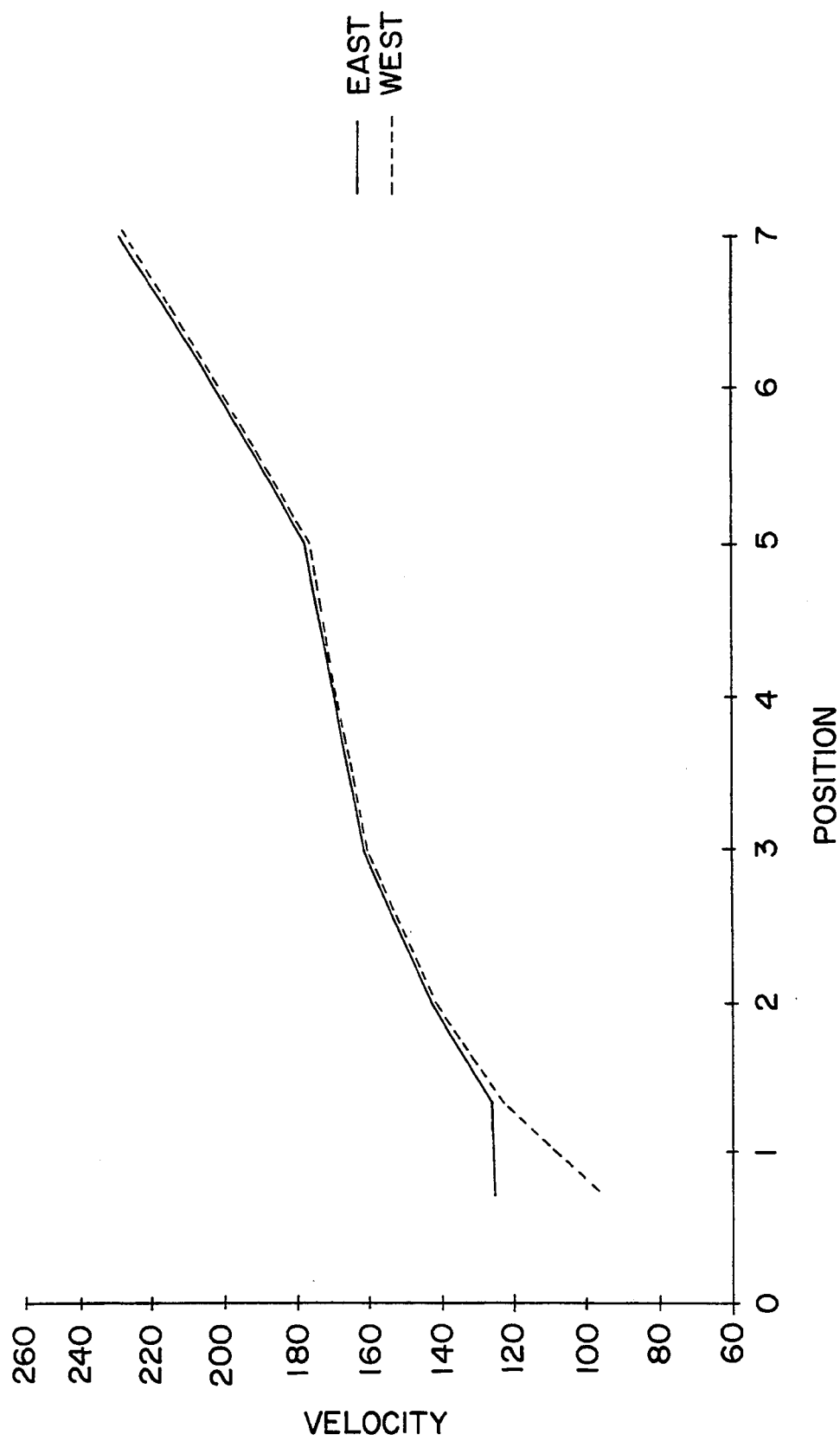

FIG. 10 illustrates the results of utilizing the reactor configuration of FIG. 1 with a larger baffle located in the same position as baffle 16. This baffle is a quarter moon shaped baffle having a circumference approximately half the circumference of the flow pipe and is more clearly illustrated in FIGS. 18-20; which will be more particularly described hereinbelow. It can be seen from FIG. 10 that the newly-installed flow baffle at position 16 results in a very close correlation in flow velocities between the east side and west side of the reactor and tends to flatten out the flow velocity gradients vertically from position 1 to approximately position 5.

Figure 11:
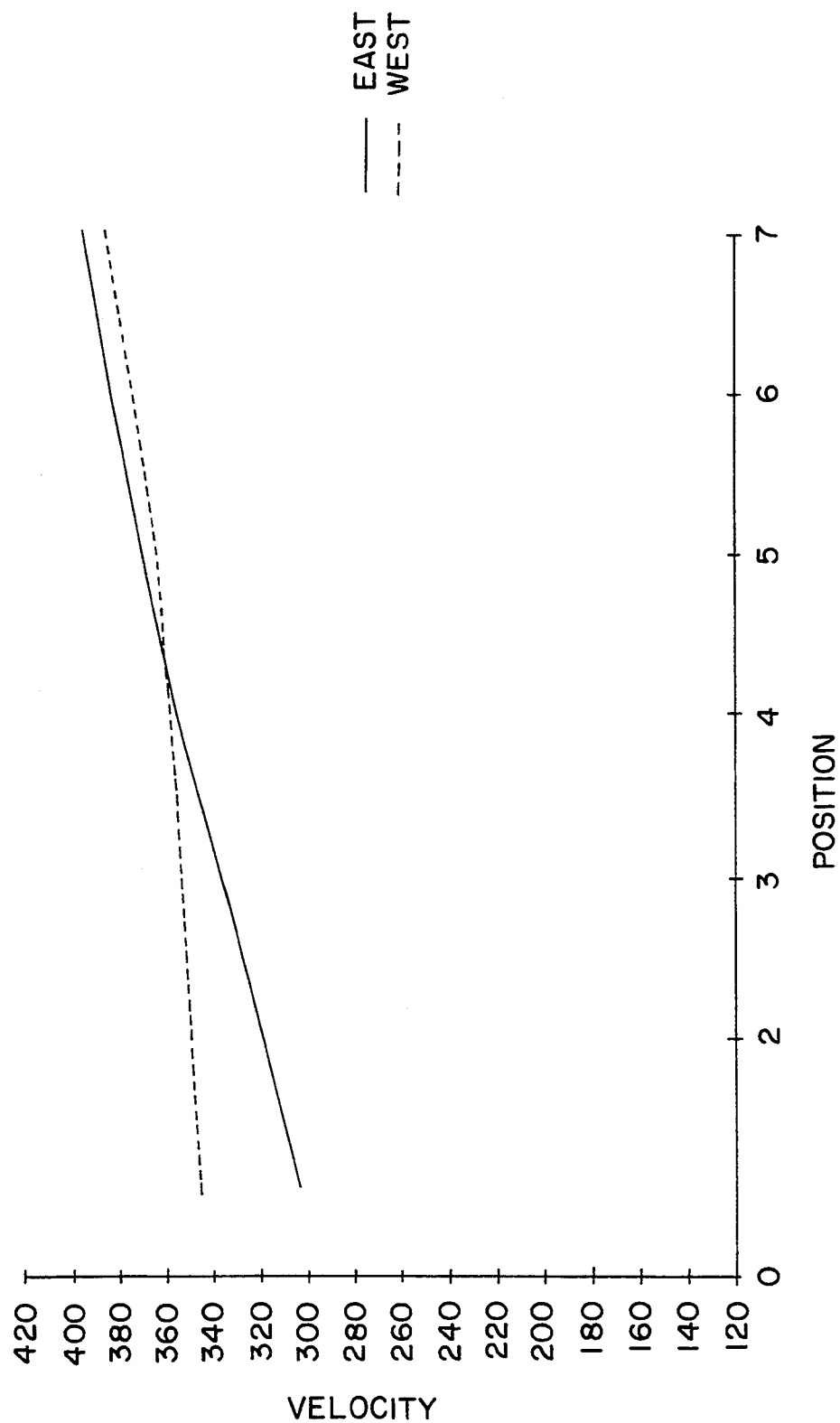

FIG. 11 is a graphic illustration of the flow velocities plotted utilizing the reactor design illustrated in FIG. 6 wherein the displacement member for 412 has been shortened by approximately one-fourth to one-third of its length, with the removal of the displacement member occurring at the bottom of the reactor and with the top of the displacement member remaining substantially in the same position as the configuration of FIG. 1. From FIG. 11 it can be seen that a slight discrepancy in flow velocities from east to west has been reestablished in the reactor, which discrepancy is not of sufficient magnitude to degrade the catalyst life, but on the other hand a very substantial decrease in flow velocity gradients in a vertical direction is achieved with reactor design of FIG. 6. For example, the average flow velocity at point 1 is approximately 320 and the average flow velocity at the very top portion of the reactor has only risen to approximately 390, an increase of only about twenty percent. The configuration of FIG. 11 would be very advantageous but is it desirable to reduce the east to west flow gradient at the lower end of the reactor from the amount illustrated in FIG. 11.

Figure 12:
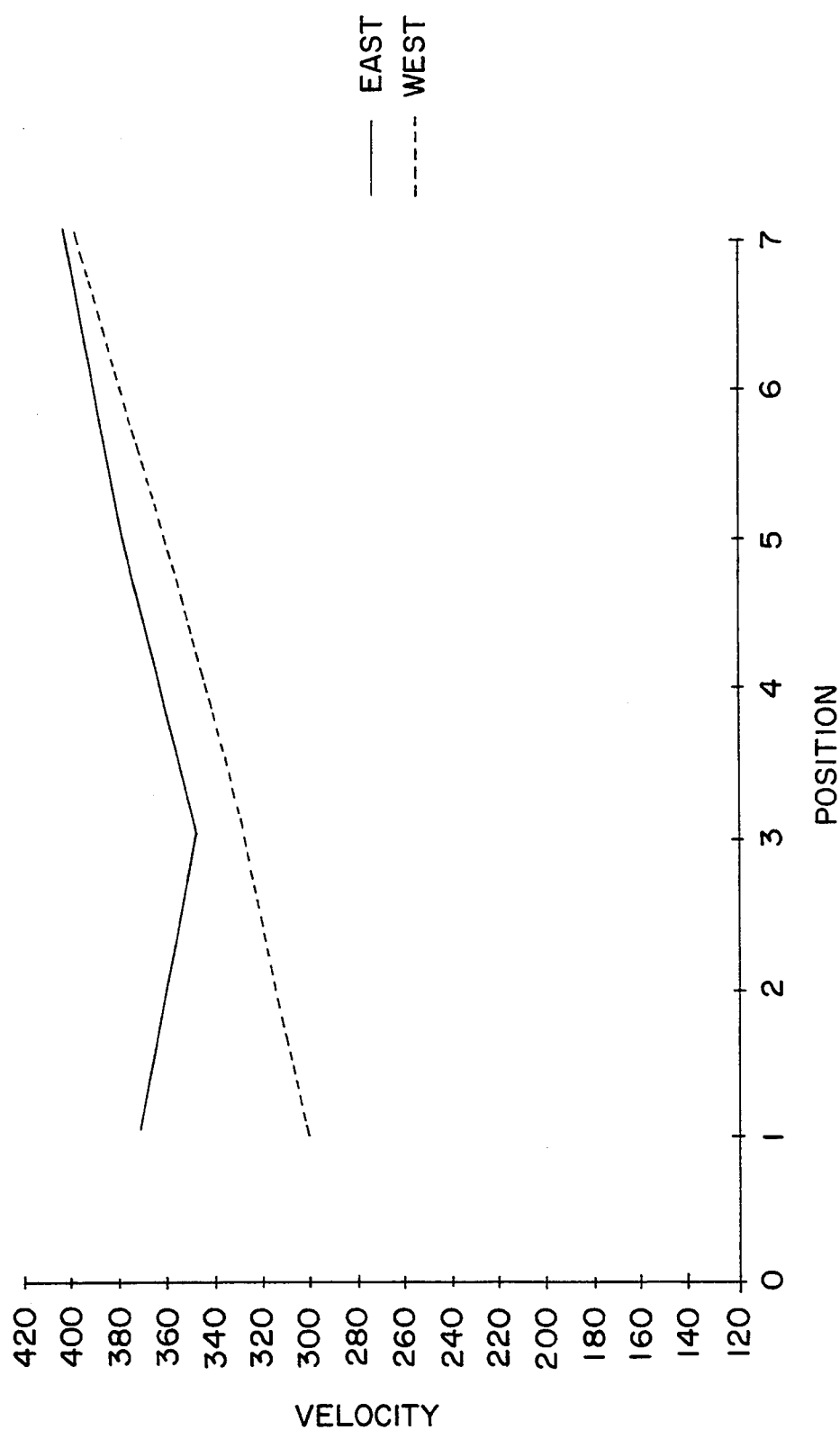

FIG. 12 illustrates flow velocity tests in a reactor configuration similar to FIG. 6 except that the displacement member 412 has been totally removed to test the effect of no displacement member. From this test it can be seen that a large discrepancy in east-west velocities occurs at points 1, 2 and 3 in the order of thirty percent or more.

Figure 13:
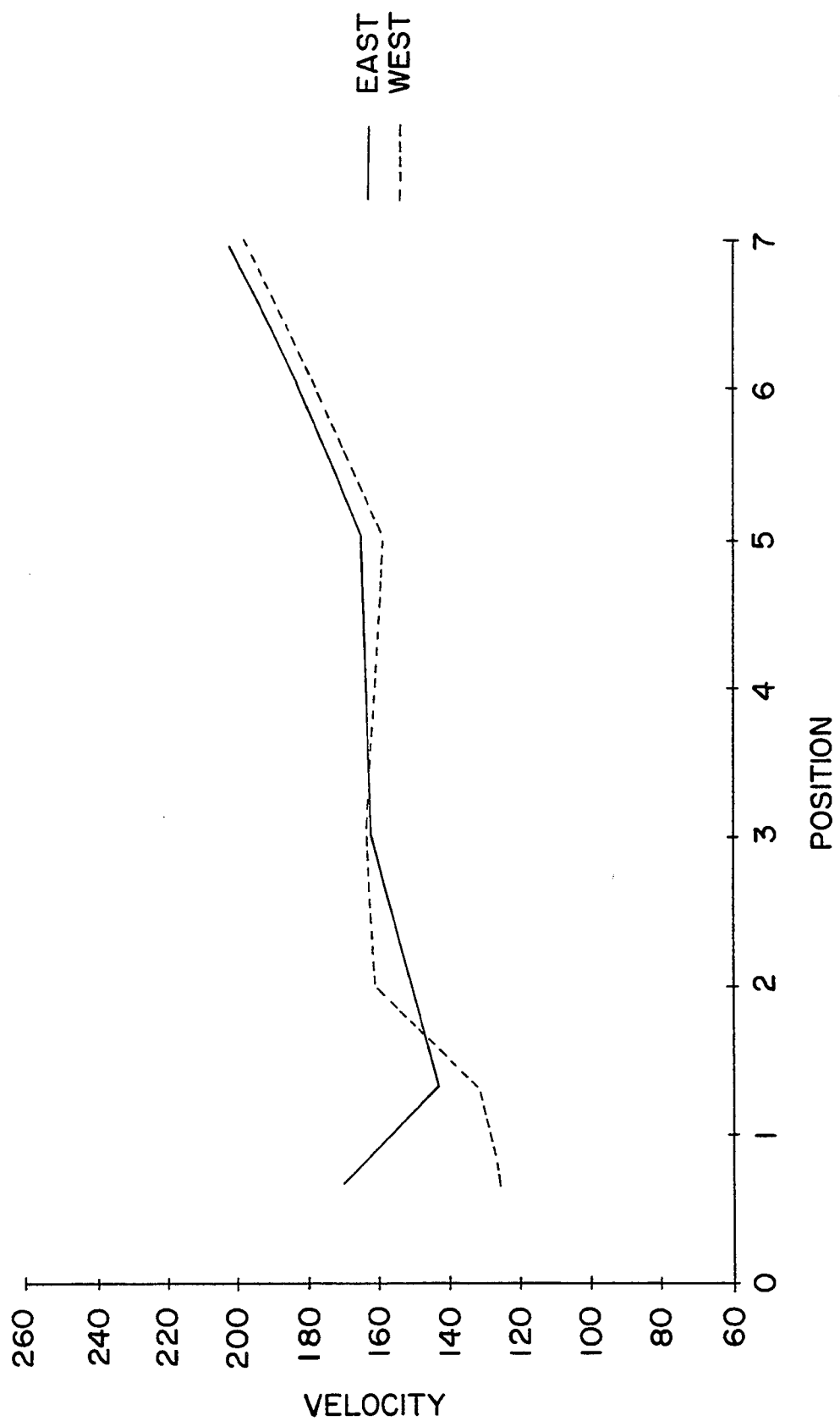

FIG. 13 illustrates the graphically the flow velocities in the configuration illustrated in FIG. 3. In this reactor configuration a relatively desirable overlap of the east-west flow velocities indicates very little flow velocity gradient transversely across the reactor. Also the relative flatness of the two curves indicates a very acceptable flow gradient vertically from position 1 to position 7. Going from approximately 150 only to approximately 220, a change of only 70.

Figure 14:
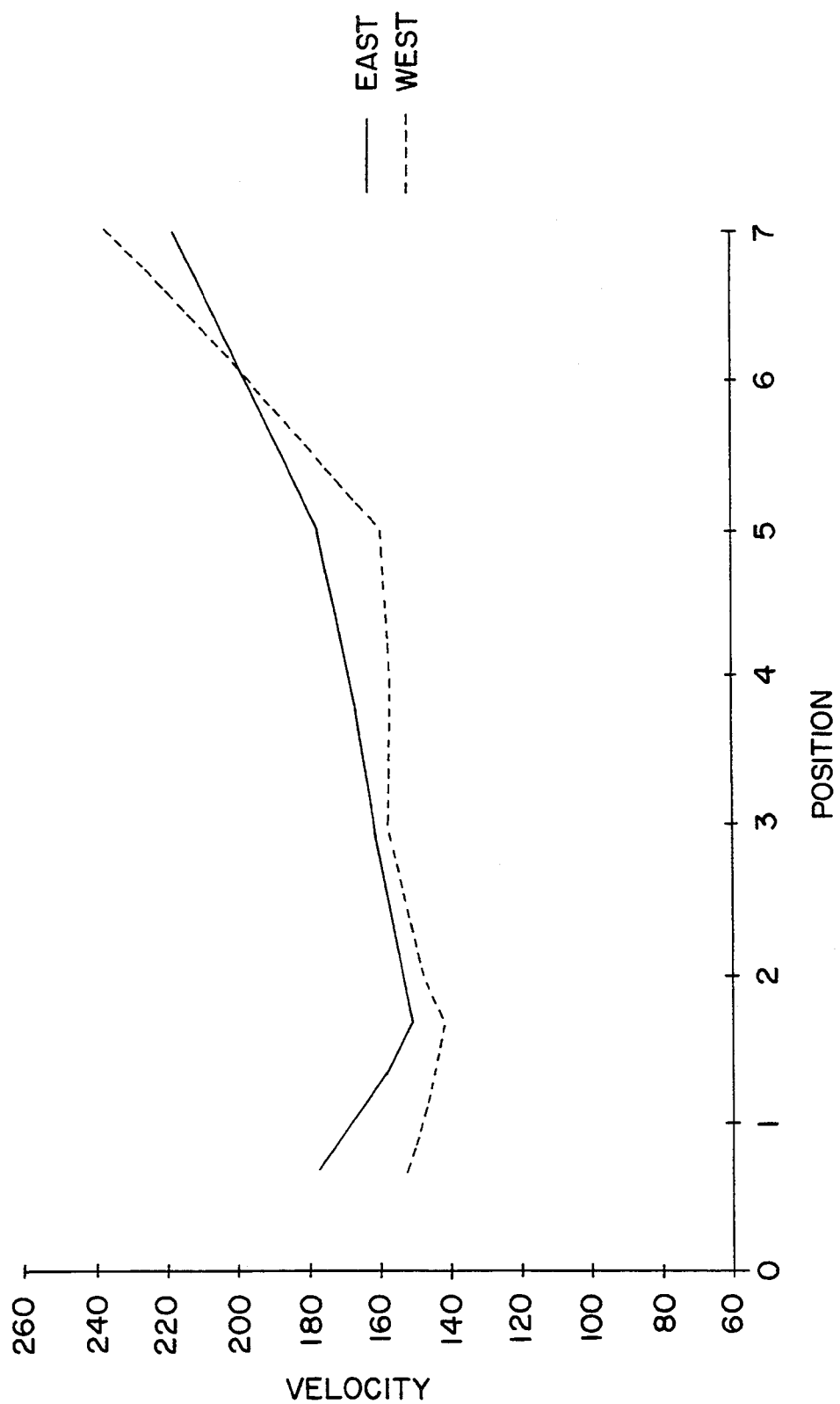

FIG. 14 is a graphic illustration of the flow velocity gradients in the reactor configuration disclosed in FIG. 4 and is not as desirable as that of the previous configuration since there is a measurable flow gradient in the east-west direction and a very measurable flow gradient between positions 5 and 7.

Figure 15:
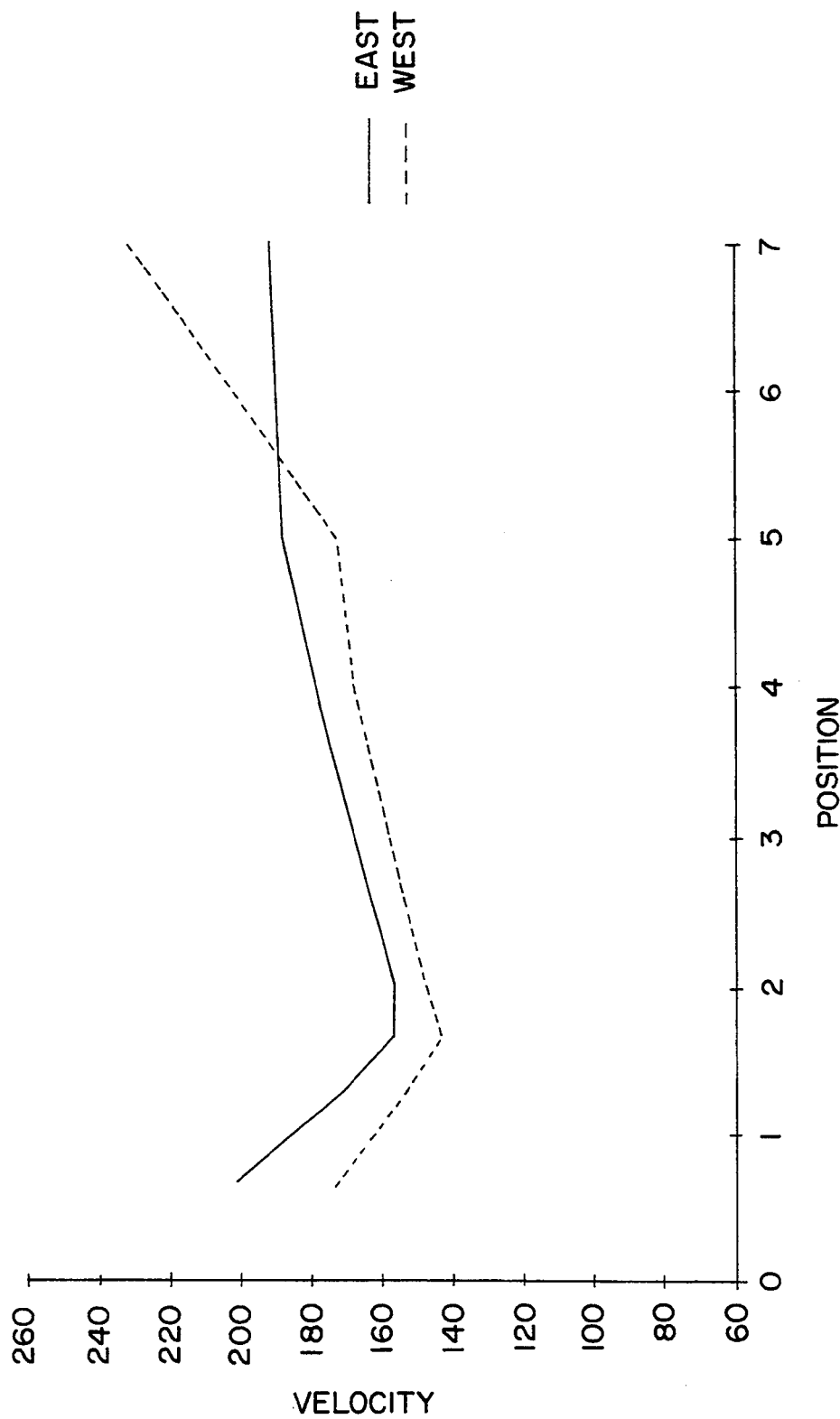

FIG. 15 is a graphic illustration of the flow velocities measured in the reactor having a configuration as illustrated in FIG. 5. In this reactor configuration the east-west flow gradients remain relatively small throughout the entire length of the catalyst bed and the average flow velocity from position a to position 7 goes from approximately 190 to approximately 220. This appears to be the most desirable configuration for overall average flow velocity consistency. In this configuration the displacement member has approximately one-fourth to one-third of the lower cylindrical portion replaced by a parabolic portion of consistent parabolic cross sectional area.

Figure 16:
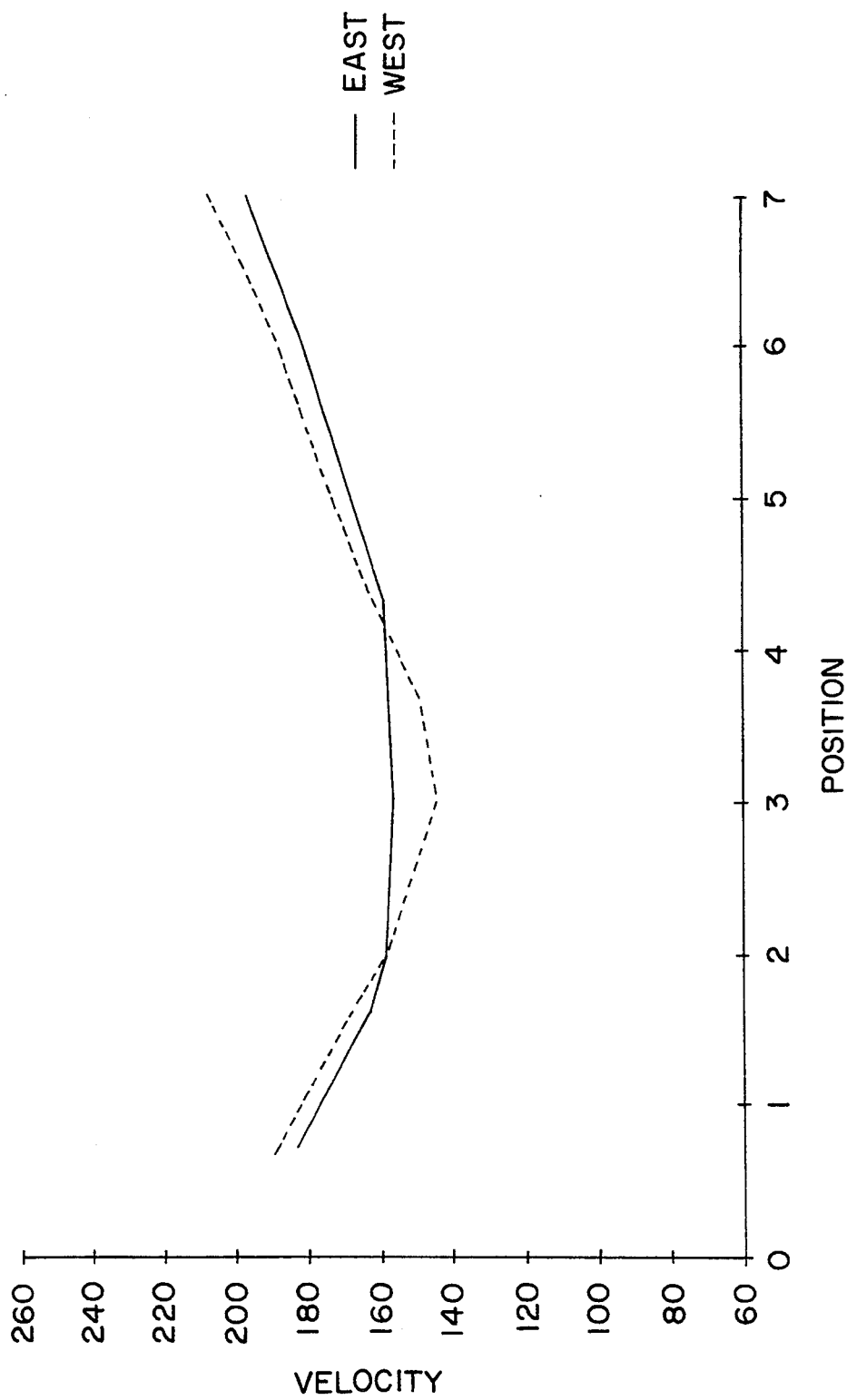

FIG. 16 is a graphical illustration of the same reactor configuration of FIG. 6 wherein the displacement member 412 has been shortened by approximately one-fourth to one-third of its length, but the difference being that the flow baffle 16 has been replaced by the improved baffle design described hereinbelow with respect to FIGS. 18-20. Although this configuration represents an improvement over the configuration of FIG. 1, there is still an appreciable flow gradient from position 1 to position "c" and a second gradient from position "c" to position 7.

Figure 17:
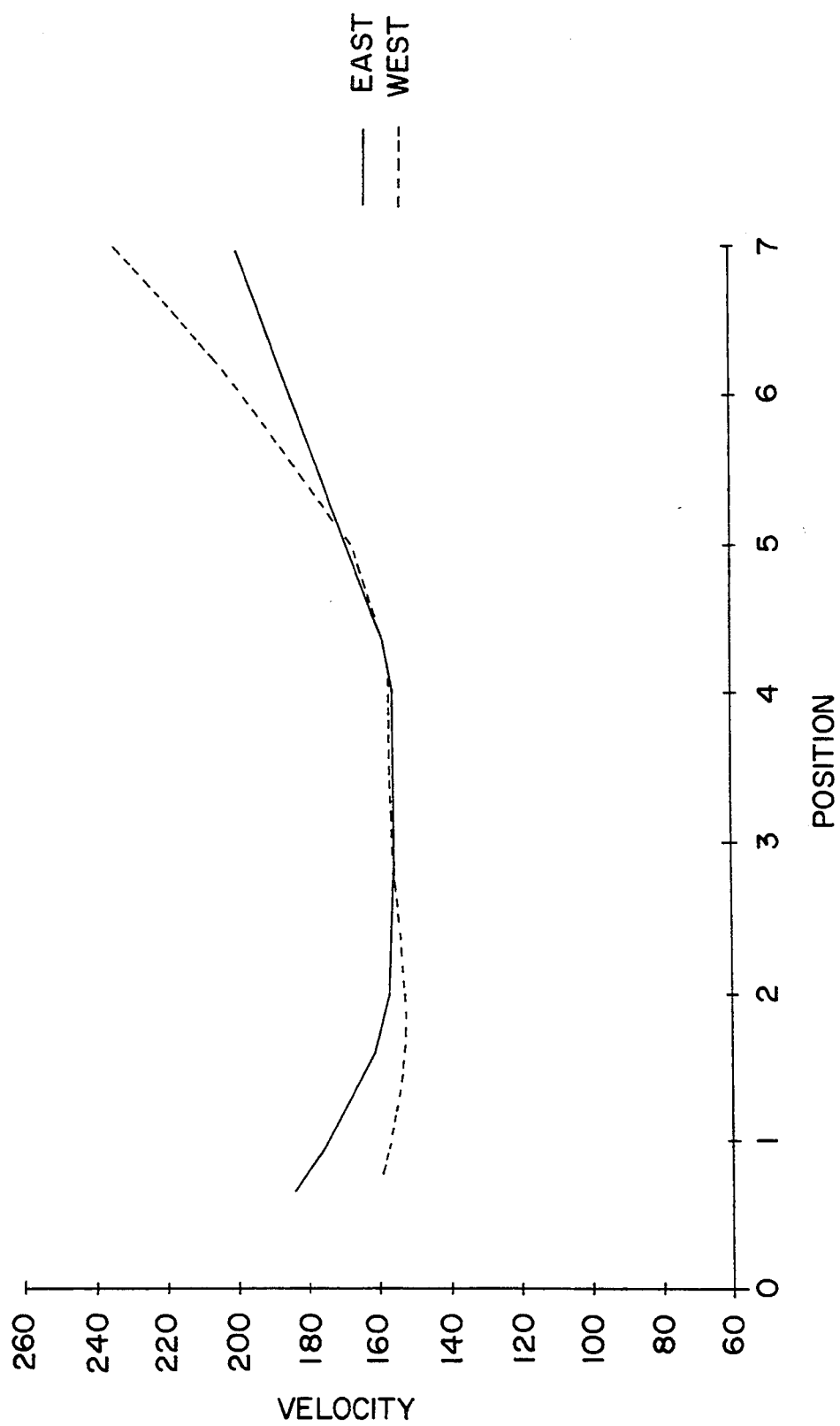

FIG. 17 is a graphical representation of the flow characteristics of the reactor of configuration FIG. 4 utilizing the new flow baffle as described hereinbelow. The results of this configuration indicate that from positions 2 to 5, there is very close correspondence between the east-west flow gradients as well as very close correspondence in a vertical direction between these positions. Unfortunately, from position 5 to position 7 there is a relatively high increase in flow velocity and an increasing spread in east-west flow gradient.

Figure 18:
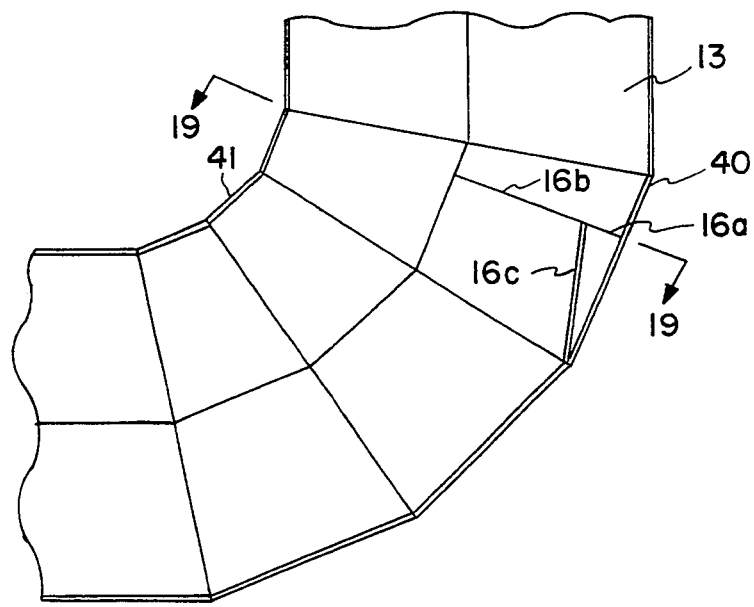
FIG. 18 is a cross sectional side view of the inlet pipe to the reactor with the baffle installed according to the present invention.

FIG. 18 is an enlarged cross sectional side view of the flow pipe 13 as illustrated and described in each of the previous figures. In FIG. 18, flow pipe 13 is shown making the right angle bend and having an outer radius 40 and an inner radius 41. In the upper half of outer radius 40 there is an improved baffle design 16a having a vertical quarter-moon shape 16b and a transverse support bracket 16c attached permanently thereto and to the outer radius 40. It should be noted that each of the segmented sections of pipe 13 preferably has a circular cross sectional shape as illustrated in FIG. 19.

Figure 19:
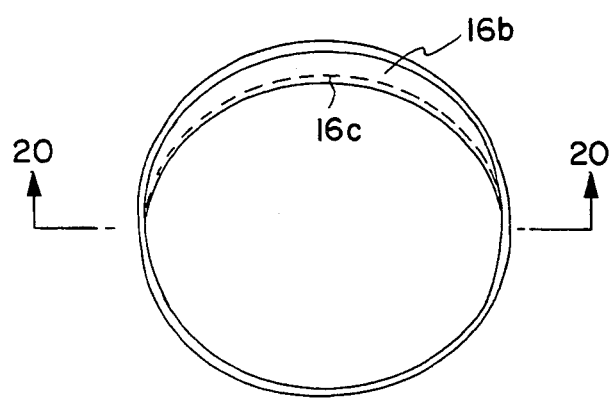
FIG. 19 is a cross sectional view taken at line A—A of FIG. 18 of the same apparatus.

Referring now to FIG. 19, the vertical quarter-moon baffle plate 16b is illustrated in the endview taken at line A—A of FIG. 18. Likewise, the attachment of the radiused semicylindrical support bracket 16c can be seen in phantom in FIG. 19 attached to baffle plate 16b. Support plate 16c serves to act as a semicircular "ramp" to smooth the flow of feed gas through the pipe 13 and direct it in a more upwardly direction to offset the effects of the relatively sharp right angle bend in pipe 13.

Figure 20:
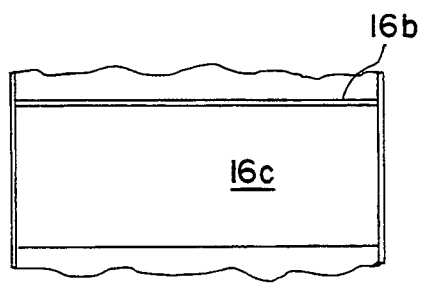
FIG. 20 is another cross sectional view of the apparatus taken at line B—B of FIG. 19.

FIG. 20 is a cross sectional side view of the baffle plate 16a showing a top view of the baffle plate taken at line B—B of FIG. 19 and a relatively flat top view of the ramp or support plate 16c.

Thus, the present invention, as disclosed in the aforementioned drawings and descriptions corresponding thereto, provides means and apparatus for the dehydrogenation of ethylbenzene to styrene, which process and apparatus enjoy the advantages of extended catalyst life and closer control of flow velocities at various points across and up-and-down the reactor cross-sectional configuration. Conventional reactors suffer from short catalyst life due to non-consistent flow velocities across varying sections of the catalyst beds. Radioactive tracer studies of these reactors indicat a severe gradient in the flow velocities across the cross-sectional configuration of the reactor. Also, flow disruptions and flow variances appear to be generated in the inlet line to the reactor.

It was discovered that the conventional inlet line configuration in the reactor caused a flow velocity gradient from east to west across the reactor. Furthermore, it was also discovered that flow velocities through the top of the catalyst bed were in the range of one and one-half to two and one-half times higher than those across the bottom of the bed. Thus, it was realized that utilization of the catalyst in the reactor was far from uniform, which in turn contributed directly to much shorter than expected catalyst life.

As a result, the present invention discloses reactor configurations that almost totally eliminate the east-west flow velocity gradients and substantially reduce the north-south flow velocity gradients. This is achieved by the use of a single baffle design located at a particularly advantageous point in the inlet flow pipe and used in conjunction with unique designs and sizes of the central coaxially located displacement members. Of the most pertinent and advantageous designs appears to be those of FIGS. 3, 5 and 6. Of these three designs, it is believed that that of FIG. 5 is the most advantageous and offers the greatest improvement in consistent flow velocities, both east-west and north-south across the reactor configuration. Although the parabolic displacement member configuration is the most preferred embodiment, it is apparent that several other disclosed configurations approach the efficiency and optimization of flow velocities of this design. For example, the shortened displacement member having approximately one-fourth to one-third of the lower end removed, and retaining its general cylindrical shape (as evidenced by the flow velocities charted in the graph of FIG. 16), approaches the flow efficiency of the previous preferred embodiment.

In typical operation, ethylbenzene feedstock is supplied to the reactor vessels via feed supply line 13 through inlet area $A_1$. From there the feed material flows into annular area $A_2$ located radially inside the catalyst bed 19. The feed gas then flows radially outward into outer annular area $A_3$, passing through the catalyst where it is dehydrogenated to styrene. Operating conditions in the reactor are preferably in the range of about 900°–1225° F. temperature, and about 8–22 PSIA pressure. Flow velocities in the reactor range from about 100 to 400 fps, with a preferred overall flow veolicity through the reactor of around 200 to 300 fps.

Although certain preferred embodiments of the present invention have been herein described in order to provide an understanding of the general principles of the invention, it will be appreciated that various changes and innovations can be effected in the described dehydrogenation reactor assembly without departing from these principles. For example, whereas the preferred embodiment is described as a partial paraboloid, it is obvious that other similar shapes such as ogive could be substituted for the paraboloid. Also, it is apparent that different baffling shapes could be utilized in the inlet line to achieve east-west flow normalization. Other changes would be apparent to one skilled in the art and therefore the invention is declared to cover all changes and modifications of the specific examples of the invention herein disclosed for purposes of illustration which do not constitute departures from the spirit and scope of the invention.

The embodiment of the present invention in which an exclusive property or privilege is claimed are defined as follows:

1. In a gas flow catalyst bed reactor assembly having an ell-shaped inlet tube for radial gas flow across an annular catalyst bed surrounding, and displaced a distance from a coaxial central cylindrical displacing member, the improvement comprising:

said inlet tube having a flow control baffle attached to the inside wall of said inlet tube at a point on the outer radius of said ell, said baffle comprising a semi-circular arcuate vertical plate and a curved ramp, a semi-circular portion of said vertical plate attached to the inside wall of said tube, said ramp attached to said plate at the downstream flow side and said inlet wall on the upstream flow side of said plate.

* * * * *